(12) United States Patent
Hetrick et al.

(10) Patent No.: US 11,473,064 B2
(45) Date of Patent: Oct. 18, 2022

(54) HYBRID ALPHAVIRUS-SARS-COV-2 PARTICLE AND METHODOLOGY OF MAKING AND USING SAME

(71) Applicant: GEORGE MASON RESEARCH FOUNDATION, INC., Fairfax, VA (US)

(72) Inventors: Brian Hetrick, Manassas, VA (US); Yuntao Wu, Manassas, VA (US)

(73) Assignee: George Mason Research Foundation, Inc., Fairfax, VA (US)

( * ) Notice: Subject to any disclaimer, the term of this patent is extended or adjusted under 35 U.S.C. 154(b) by 0 days.

(21) Appl. No.: 17/505,496

(22) Filed: Oct. 19, 2021

(65) Prior Publication Data

US 2022/0119776 A1   Apr. 21, 2022

Related U.S. Application Data

(60) Provisional application No. 63/183,189, filed on May 3, 2021, provisional application No. 63/118,787, filed on Nov. 27, 2020, provisional application No. 63/094,029, filed on Oct. 20, 2020.

(51) Int. Cl.
| | | |
|---|---|---|
| *A61K 39/00* | (2006.01) | |
| *C12N 15/86* | (2006.01) | |
| *C12N 7/00* | (2006.01) | |
| *A01N 63/00* | (2020.01) | |
| *A61K 39/12* | (2006.01) | |
| *C12N 9/02* | (2006.01) | |
| *A61K 39/215* | (2006.01) | |
| *C12Q 1/6897* | (2018.01) | |

(52) U.S. Cl.
CPC ............ *C12N 7/00* (2013.01); *A61K 39/215* (2013.01); *C12N 9/0069* (2013.01); *C12N 15/86* (2013.01); *C12Q 1/6897* (2013.01); C12N 2770/20023 (2013.01); C12N 2770/20071 (2013.01); C12N 2770/36121 (2013.01); C12N 2770/36143 (2013.01)

(58) Field of Classification Search
CPC .............. A61K 2300/00; A61K 38/177; A61K 38/178; A61K 38/191; A61K 38/193
See application file for complete search history.

(56) References Cited

U.S. PATENT DOCUMENTS

2011/0002958 A1   1/2011   Perri et al.
2018/0356394 A1   12/2018  Novobrantseva et al.

OTHER PUBLICATIONS

McKay et al., "Self-amplifying RNA SARS-CoV-2 lipid nanoparticle vaccine candidate induces high neutralizing antibody titers in mice", Nature Communications, 2020:1-7.*
Erasmus et al., "An alphavirus-derived replicon RNA vaccine induces SARS-CoV-2 neutralizing antibody and T cell responses in mice and nonhuman primates", Science Translational Medicine, 2020:1-16.*
Paul F. McKay et al., "Self-amplifying RNA SARS-CoV-2 lipid nanoparticle vaccine candidate induces high neutralizing antibody titers in mice," Nature Communications, Jul. 9, 2020.
Invitation to Pay Additional Fees in International Application No. PCT/US21/55666, dated Dec. 23, 2021.
International Search Report and Written Opinion for PCT/US21/55666, dated Mar. 15, 2022.

* cited by examiner

*Primary Examiner* — Barry A Chestnut
(74) *Attorney, Agent, or Firm* — Pilloff Passino & Cosenza LLP; Sean A. Passino; Rachel K. Pilloff

(57) ABSTRACT

Timely development of vaccines and antiviral drugs is critical to control the COVID-19 pandemic. Current methods for quantifying vaccine-induced neutralizing antibodies involve the use of pseudoviruses, such as the SARS-CoV-2 spike protein (S) pseudotyped lentivirus. However, these pseudoviruses contain structural proteins foreign to SARS-CoV-2, and require days to infect and express reporter genes. Here, the present application discloses composition and methodology for making and using a new hybrid alphavirus-SARS-CoV-2 (Ha-CoV-2) particle for rapid and accurate quantification of neutralization antibodies and viral variants.

20 Claims, 7 Drawing Sheets

Figure 6

HYBRID ALPHAVIRUS-SARS-COV-2 PARTICLE AND METHODOLOGY OF MAKING AND USING SAME

CROSS-REFERENCE TO RELATED APPLICATIONS

The present application claims priority benefit of U.S. Provisional Application No. 63/094,029, filed Oct. 20, 2020; U.S. Provisional Application No. 63/118,787, filed Nov. 27, 2020; and U.S. Provisional Application No. 63/183,189, filed May 3, 2021; each application is incorporated herein by reference in its entirety.

INTRODUCTION

Severe acute respiratory syndrome coronavirus 2 (SARS-CoV-2) is a rapidly spreading, novel beta-coronavirus that is causing the ongoing global pandemic of coronavirus disease 2019 (COVID-19)[17-21]. SARS-CoV-2 has caused over 140 million infections and 3 million deaths globally as of April 2021. Antiviral drugs and neutralizing antibodies are effective to combat the pandemic. In particular, neutralizing antibodies, induced by vaccines or by the virus, can play a critical role in controlling and preventing infection. Currently, only one FDA-approved drug, remdesivir, is available to reduce hospital stay[1]; several vaccines have recently shown significant results in phase III clinical trials[2-6], and been approved for emergency use, with one vaccine receiving full FDA approval as of August 2021. Nevertheless, the effectiveness of vaccines needs to be continuously monitored for the induction of neutralizing antibodies against evolving viral variants.

Current antiviral drug screening and quantification of neutralizing antibodies rely on the use of SARS-CoV-2 pseudoviruses[7-14]. The use of live virus requires biosafety level (BSL) 3 facility and practice, which limits large-scale testing and analyses in common laboratories. Both lentivirus and vesicular stomatitis virus (VSV), pseudotyped with the SARS-CoV-2 S protein, are used in cell-based neutralization assays and in antiviral drug screening[8-11]. SARS-CoV-2 contains four structural proteins: the spike protein (S), the membrane protein (M), the envelope protein (E), and the nucleocapsid protein (N)[22,23]. S is the major viral protein responsible for virus attachment and entry to target cells[24-26], and thus, is commonly used to pseudotype viruses. Nevertheless, both VSV- and lentiviral-based pseudoviral particles contain only the S protein, and the major viral structural components are foreign to SARS-CoV-2, which may affect viron properties in receptor binding and responses to antibody neutralization[15]. In addition, an important issue for the VSV-based pseudovirus is the presence of residual VSV virus, which can result in high rates of false-positive results[27]. Furthermore, the use of lenti-pseudoviruses for neutralization assay is time consuming, and requires 2 to 3 days to infect and generate reporter signals[7-11].

SUMMARY

In one aspect, there is a hybrid particle, comprising: a) a RNA genome derived from an alphavirus; and b) at least one SARS-CoV-2 structural protein, wherein said structural protein is a spike protein (S), a membrane protein (M), an envelope protein (E), and the nucleocapsid protein (N).

In one embodiment, the hybrid particle is a non-replicating particle.

In another embodiment, the RNA genome derived from the alphavirus comprises a reporter gene or a gene of interest. In a further embodiment, the reporter gene comprises a GFP gene or a luciferase gene.

In another embodiment, the RNA genome comprises: a) 5' untranslated region; b) an open-reading frame coding for a non-structural proteins (nsp) 1-4; c) a reporter gene or a gene of interest; d) 3' untranslated region; and e) a poly(A) tail. In a further embodiment, the RNA genome comprises a SARS-CoV-2 packaging signal, wherein the SARS-CoV-2 packaging signal is downstream of the reporter gene.

In another embodiment, the hybrid particle is SARS-CoV-2 virus-like particles (VLPs).

In another embodiment, the hybrid particle targets a cell expressing ACE2.

In another embodiment, the hybrid particle comprises two SARS-CoV-2 structural proteins, wherein said structural proteins comprise S and E.

In another embodiment, the hybrid particle comprises four SARS-CoV-2 structural proteins, wherein said structural proteins comprise S, E, M, and N. In a further embodiment, the hybrid particle has a direct correlation in a IC50 value with SARS-CoV-2.

In another aspect, a method, comprising (a) co-transfecting a first vector encoding at least one SARS-CoV-2 structural protein and a second vector comprising an RNA genome derived from an alphavirus, wherein the alphavirus RNA genome comprises (i) a DNA promoter at a 5' end, (ii) a first untranslated region (iii) an open reading frame coding a nonstructural protein from an alphavirus, (iv) a reporter gene, (v) a SARS-CoV-2 packaging signal sequence, (vi) a viral subgenomic RNA promoter, (vii) a gene of interest (viii) a second untranslated region, and (ix) a polyA tail; and (b) generating a hybrid particle, wherein the hybrid particle comprises an alphavirus RNA genome and at least one SARS-CoV-2 structural protein.

In one embodiment, a method further comprises infecting a target cell with the hybrid particle, wherein said target cell expresses ACE2.

In another embodiment, expression of the reporter gene is capable of producing a signal that facilitates detection and quantification of an infection. In a further embodiment, the signal is read after about 2 to about 72 hours following infection by the hybrid particle.

In another aspect, a method for detecting a subject's antibody response to one or more SARS-CoV-2 variants, comprising a) incubating a serum sample from said subject with the hybrid particle; b) introducing the incubated hybrid particle into a cell comprising ACE2; and
c) detecting reporter gene expression in said cell, wherein reporter gene expression is indicative of the subject having no neutralizing antibodies to block viral infection of the cell, and
no reporter gene expression is indicative of the subject having antibodies that block viral infection of the cell.

In one embodiment, the method further comprises administering an antibody, vaccine, or treatment to the subject that does not have neutralizing antibodies to one or more SARS-CoV-2 variants.

In another embodiment, a composition comprises the hybrid particle with at least one SARS-CoV-2 structural protein, wherein said structural protein is a spike protein (S), a membrane protein (M), an envelope protein (E), and the nucleocapsid protein (N). In a further embodiment, the composition is a vaccine or a particle that can initiate an immune response.

In another embodiment, a composition comprises a hybrid particle comprising four SARS-CoV-2 structural proteins, wherein said structural proteins comprise S, E, M, and N. In a further embodiment, the composition is a vaccine or a particle that can initiate an immune response.

In another embodiment, a composition comprises the hybrid particle, wherein said composition is a vaccine or a particle that can initiate an immune response.

In another aspect, a hybrid vector comprises (i) a DNA promoter at a 5' end, (ii) a first untranslated region at the 5' end, (iii) an open reading frame coding a nonstructural protein from an alphavirus, (iv) a SARS-CoV-2 packaging signal sequence, (v) a viral sub-genomic RNA promoter, (vi) a gene of interest, (vii) a second untranslated region at a 3' end, and (viii) a polyA tail at the 3' end. In some embodiments, the hybrid vector further comprises a reporter gene. In some embodiments, the nonstructural protein comprises a RNA polymerase and an associated factor. In some embodiments, the alphavirus comprises a semiliki forest virus. In some embodiments, the hybrid vector is configured to express a transgene in a cell. In some embodiments, the hybrid vector is configured to facilitate screening of an anti-viral drug, an antibody, and/or an anti-viral protein.

In some embodiments, a method comprises (a) co-transfecting a first vector encoding a structural component of a SARS-CoV-2 and a second vector comprising a replicon vector from a positive-sense RNA virus or an alphavirus replicon vector or a hybrid vector. The hybrid vector comprises: (i) a DNA promoter at a 5' end, (ii) a first untranslated region, (iii) an open reading frame coding a nonstructural protein from an alphavirus, (iv) a SARS-CoV-2 packaging signal sequence, (v) a viral subgenomic RNA promoter, (vi) a gene of interest, (vii) a second untranslated region, and (viii) a polyA tail. The method also generates a hybrid alphavirus-SARS-CoV-2 (HAYS) particle, wherein the HAYS particle comprises an alphavirus RNA genome and the structural component from the SARS-CoV-2. In some embodiments, the structural component comprises at least one selected from a spike protein (S), a membrane protein (M), a nucleocapsid protein (N) and an envelope protein (E). In some embodiments, the alphavirus replicon vector and the hybrid vector and the replicon vector from the positive-sense RNA further comprise a reporter gene. In some embodiments, the nonstructural protein comprise a RNA polymerase and an associated factor. In some embodiments, the HAYS particle is configured to infect a target cell, wherein the target cell expresses ACE2. In some embodiments, expression of the reporter gene is configured to produce a signal that facilitates detection and quantification of an infection.

In some embodiments, the signal is read after 2 to 72 hours of infection by the HAYS particle. In some embodiments, the method is configured to test a SARS-CoV-2 viral entry inhibitor and/or a neutralizing antibody for SARS-CoV-2 and/or screening for an anti-viral drug and/or screening for an anti-viral protein. In some embodiments, the viral entry inhibitor comprises an Arbidol.

In some embodiments, a product comprising a hybrid alphavirus-SARS-CoV-2 (HAYS) particle comprising an alphavirus RNA genome and a structural component from a SARS-CoV-2. In some embodiments, the HAYS particle is formed by cotransfection of a first vector encoding a structural component of the SARS-CoV-2 and a second vector comprising a replicon vector from a positive-sense RNA virus or an alphavirus replicon vector or a hybrid vector comprises: (i) a DNA promoter at a 5' end, (ii) a first untranslated region at the 5' end, (iii) an open reading frame coding a nonstructural protein from an alphavirus, (iv) a SARS-CoV-2 packaging signal sequence, (v) a viral subgenomic RNA promoter, (vi) a gene of interest, (vii) a second untranslated region at a 3' end, and (viii) a polyA tail at the 3' end, wherein the HAYS particle is configured to identify a SARS-CoV-2 viral entry inhibitor and/or a neutralizing antibody for the SARS-CoV-2. In some embodiments, the hybrid vector and the alphavirus replicon vector and the replicon vector from the positive-sense RNA further comprise a reporter gene. In some embodiments, the reporter gene is configured to produce a signal that facilitates detection and quantification of an infection caused by the HAYS particle. In some embodiments, the structural component comprises at least one selected from a spike protein (S), a membrane protein (M), a nucleocapsid protein (N) and an envelope protein (E).

The instant SARS-CoV-2 VLP packaged replicons are a substantial advancement in the field of virus-like-particles and nanoparticle-based technologies. These hybrid VLPs are particularity useful in modeling infections of SARS-CoV-2 for novel drug and vaccine development. This is a great advancement in modeling the infection pathway for coronaviruses and could be easily adapted to other virus families. This is also an advancement in immunotherapy and vaccine development as the transported replicons can stimulate the innate immune response and the gene of interest can produce a target antigen.

The hybrid alphavirus replicon VLPs are a great model for novel drug discovery and antibody-neutralization assay. The particles can be produced cheaply and can be used to quickly evaluate viral entry inhibitors. The VLPs can be sold directly to labs working on drug discovery.

BRIEF DESCRIPTION OF THE FIGURES

FIG. 6: Quantification of the relative infectivity of Ha-CoV-2 variants and their responses to neutralizing antibodies. (A and B) Ha-CoV-2(Luc) particles bearing the G614 mutation S or the parent D614 S were assembled, and analyzed for the incorporation of S and N in virions. (C) Ha-CoV-2(Luc)(G614) or Ha-CoV-2(D614) was used to infect target cells, and Luc expression was quantified at 5 hours. An equal level of viral particles was used for infection. Infection assays were performed in triplicates. (D) A panel of 9 S protein mutants from SARS-CoV-2 variants were used to assemble Ha-CoV-2(Luc) particles, and then used to infect target cells. The relative infectivity was quantified and normalized with the genomic RNA copies of individual Ha-CoV-2(Luc) variants. WT refers to Ha-CoV-2 derived from the original SARS-CoV-2 strain. Infection assays were performed in triplicates. (E and F) Quantification of anti-serum against Ha-CoV-2(Luc) and its variants. Convalescent plasma from an infected blood donor, before and after one dose vaccination, was quantified for inhibition of Ha-CoV-2(Luc) infection. Neutralization activities were quantified by luciferase assay at 12 hours post infection. The $IC_{50}$ was calculated using the relative percentage of infection versus serum concentration (E). The post-vaccination anti-serum was similarly quantified for the inhibition of Ha-CoV-2(Luc) variants (F).

DETAILED DESCRIPTION

Figure 1:
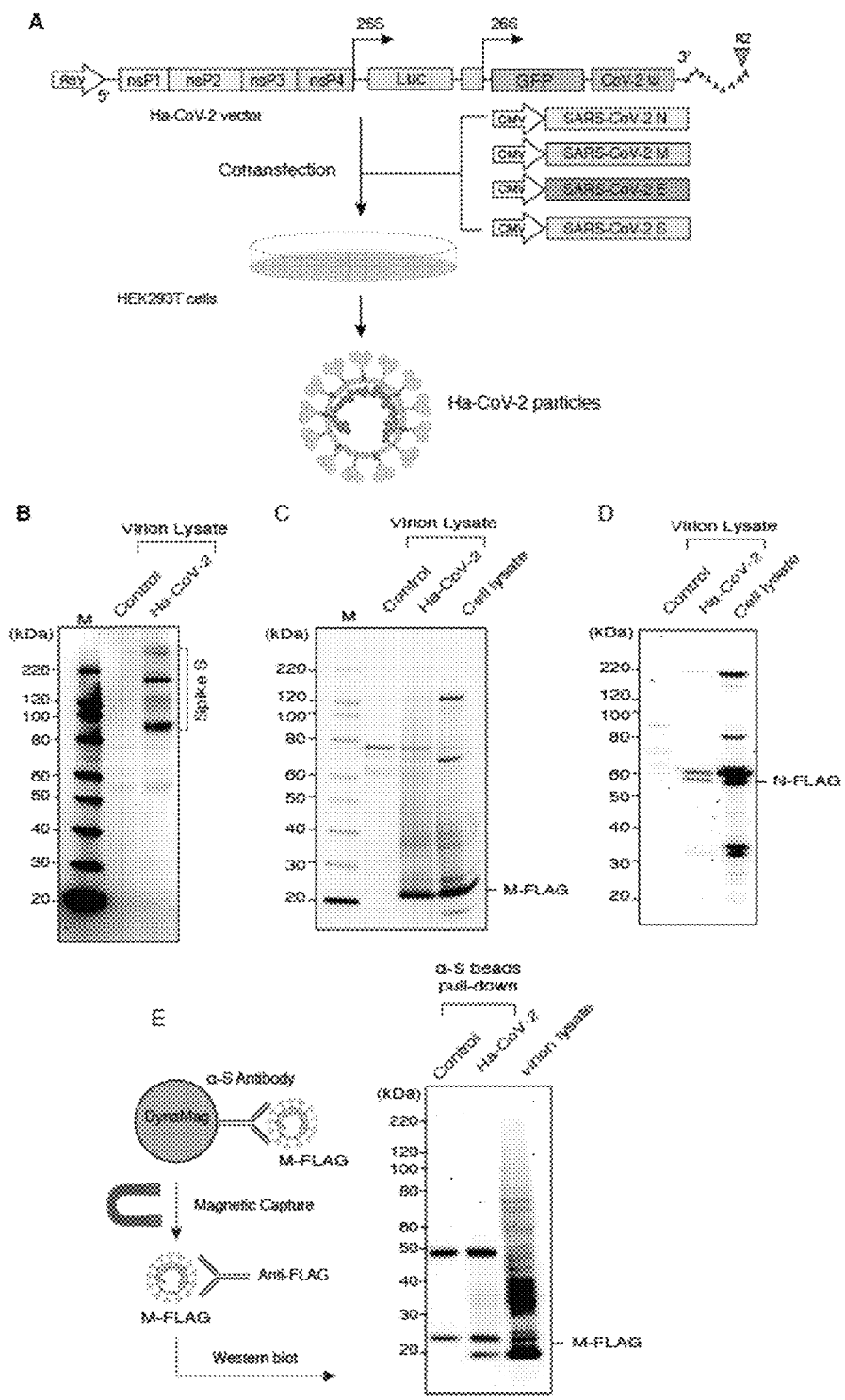
FIG. 1: Design and assembly of Ha-Cov-2 particles. (A) Illustration of the design of Ha-CoV-2 vector. The vector contains a RSV promoter that transcribes the full-length viral RNA genome to be packaged into Ha-CoV-2 particles. Shown are the 5' untranslated region followed by open-reading frames coding for nonstructural proteins (nsp) 1-4 from Semliki Forest virus (SFV), viral subgenomic promoters for Luc and GFP reporter expression, the 3' untranslated region and a poly(A) tail that is self-cleaved by the hepatitis delta virus ribozyme (RZ). The SARS-CoV-2 packaging signal is inserted in front of the 3' untranslated region. To assemble viral particles, HEK293T cells were co-transfected with Ha-CoV-2 and the vectors expressing the 4 structural proteins of SARS-CoV-2 (S, M, E, and N). HA-CoV2 particles in the supernatant were harvested at 48 hours, purified, lysed, and then analyzed by western blot using antibodies for the SARS-CoV-2 S protein (B). Control is the supernatant from cells transfected with the Ha-CoV-2 vector alone. (C and D) Particles were also assembled using FALG-tagged M and N. Particles were analyzed with western blot using an antibody against FLAG. (E) Particles in the supernatant were also captured with magnetic beads conjugated with the anti-S antibody, and then analyzed with western blot using the antibody again FLAG for FLAG-tagged M protein in the particles.

Timely development of vaccines and antiviral drugs is critical to control the COVID-19 pandemic[1-6]. Current methods for quantifying vaccine-induced neutralizing antibodies involve the use of pseudoviruses, such as the SARS-CoV-2 spike protein (S) pseudotyped lentivirus[7-14]. However, these pseudoviruses contain structural proteins foreign to SARS-CoV-2, and require days to infect and express reporter genes[15].

As explained below, the present application discloses methodology for making and using a new hybrid alphavirus-SARS-CoV-2 particle (Ha-CoV-2) for rapid quantification of neutralization antibodies and antiviral drugs. Ha-CoV-2 is a non-replicating SARS-CoV-2 virus-like particle comprising one or more authentic virus structural proteins (S, M, N, and E) from SARS-CoV-2. Ha-CoV-2 also contains a genome derived from an alphavirus-based vector[16,28], which can rapidly and robustly express reporter genes within a few hours after viral entry[28]. Furthermore, and as detailed below, Ha-CoV-2 can be used as a robust platform for rapid quantification of neutralization antibodies, viral variants, and antiviral drugs.

The present inventors provide a new hybrid alphavirus-SARS-CoV-2 (Ha-CoV-2) particle for rapid and accurate quantification of neutralization antibodies and viral variants. Ha-CoV-2 is a non-replicating SARS-CoV-2 virus-like particle, comprising one or more SARS-CoV-2 structural proteins (S, M, N, and E) and a RNA genome derived from a fast expressing alphavirus vector[16]. Ha-CoV-2 can rapidly and robustly express reporter genes, such as the genes encoding GFP or luciferase, in target cells within 3-6 hours. Further, Ha-CoV-2 provides a platform for rapid quantification of neutralization antibodies, viral variants, and antiviral drugs. In addition, as a proof-of-concept, the present inventors assembled and compared the relative infectivity of a panel of 10 Ha-CoV-2 variant isolates (D614G, P.1, B.1.1.207, B.1.351, B.1.1.7, B.1.429, B.1.258, B.1.494, B.1.2, B.1.1298), and demonstrated that these variants in general are 2-10-fold more infectious. Furthermore, by quantifying the anti-serum from an infected and vaccinated individual; the one dose vaccination with Moderna mRNA-1273 has greatly increased the anti-serum titer for approximately 6-fold. The post-vaccination serum has also demonstrated various neutralizing activities against all 9 variants tested.

These results demonstrated that Ha-CoV-2 can be used as a robust platform for rapid quantification of neutralizing antibodies against SARS-CoV-2 and its variants.

The present compositions and methodology are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The term "SARS-CoV-2 (Severe Acute Respiratory Syndrome Coronavirus 2)" as used herein refers to a strain of coronavirus that causes coronavirus disease 2019 (COVID-19), the respiratory illness responsible for the COVID-19 pandemic. SARS-CoV-2 is a positive-sense single-stranded RNA virus that is contagious in humans.

"Alphavirus" as used herein refers to a genus of more than 30 viruses in the Togaviridae family, are lipid-enveloped, positive-sense RNA viruses that are transmitted by arthropods and especially mosquitoes and that include the Mayaro virus, Semliki Forest virus, Sindbis virus, and the causative agents of chikungunya and equine encephalitis. Although the instant application discloses an alphavirus replicon as the backbone for the instant hybrid SARS-CoV-2 vector, replicons from single-stranded, positive RNA viruses of the three phyla (Kitrinoviricota, Lenarviricota, and Pisuviricota) may be used.

"Vaccine" as used herein refers to a suspension of antigens derived from viruses or bacteria that, upon administration, will produce active immunity and provide protection against those viruses or bacteria or related viruses or bacteria.

"Virus-like particles (VLPs)" as used herein refers to a molecule that closely resemble viruses but are non-infectious because they contain no viral genetic material. They can be naturally occurring or synthesized through the individual expression of viral structural proteins, which can then self-assemble into the virus-like structure. Combinations of structural capsid proteins from different viruses can be used to create recombinant VLPs.

As used herein, "Hybrid particle" refers to a hybrid alphavirus-SARS-CoV-2 viral vector (Ha-CoV-2) with at least one structural protein (S, M, N, and E) that closely resembles the wild-type virus. As used throughout the application, hybrid particle is used interchangeably with hybrid alphavirus-SARS-CoV-2 vector (HAYS) or Ha-CoV-2, the three terms are synonymous and refer to the same hybrid particle. In one embodiment, an instant Ha-CoV-2 may comprise only one structural protein (S, M, E, and N) of SARS-CoV-2. In other embodiments, an instant Ha-CoV-2 may comprise two or more structural protein (S, M, E, and N) of SARS-CoV-2. In yet other embodiments, an instant Ha-CoV-2 may comprise three or more structural protein (S, M, E, and N) of SARS-CoV-2. The hybrid particle may also comprise a reporter (GFP or Luc) replicon derived from alphavirus that can rapidly express reporter genes within hours. In some embodiments, a hybrid particle is capable of expressing high levels of transgenes in an infected target cell, thereby providing a novel platform for tracking infectivity, facilitating rapid screening of anti-viral drugs and neutralizing antibodies, as well as providing new compositions such as vaccines.

"SARS-CoV-2 structural protein" refers to viral proteins that are components of the mature assembled virus particles. They may include nucleocapsid core proteins (gag proteins), enzymes packaged within the virus particle (pol proteins), and membrane components (env proteins). Relevant here, SARS-CoV-2 has four types of structural proteins, the spike protein (S), the membrane protein (M), the envelope (E) proteins, and the nucleocapsid (N).

The term "lentivirus" as used herein is defined as a genus of retroviruses that cause chronic and deadly diseases characterized by long incubation periods, in the human and other mammalian species. The best-known lentivirus is the human immunodeficiency virus (HIV), which causes AIDS. Lentiviruses are also hosted in apes, cows, goats, horses, cats, and sheep. Recently, lentiviruses have been found in monkeys, lemurs, Malayan flying lemur (neither a true lemur nor a primate), rabbits, and ferrets. Lentiviruses and their hosts have worldwide distribution. Lentiviruses can integrate a significant amount of viral cDNA into the DNA of the host cell and can efficiently infect nondividing cells, so they are one of the most efficient methods of gene delivery.

"ACE2 receptor" as used herein refers to Angiotensin-converting enzyme 2 is an enzyme that generates small proteins by cutting up the larger protein angiotensinogen that then go on to regulate functions in the cell. ACE2 is present in many cell types and tissues including the lungs, heart, blood vessels, kidneys, liver and gastrointestinal tract. It is present in epithelial cells, which line certain tissues and create protective barriers. Using the spike-like protein on its surface, the SARS-CoV-2 virus binds to ACE2 like a key being inserted into a lock prior to entry and infection of cells. Hence, ACE2 acts as a cellular doorway a receptor for the virus that causes COVID-19.

"TMPRSS2" as used herein refers to a Transmembrane protease, serine 2 is an enzyme that in humans is encoded by the TMPRSS2 gene. Some coronaviruses, e.g., both the SARS coronavirus of 2003 and the SARS-CoV-2 are activated by TMPRSS2 and can thus be inhibited by TMPRSS2 inhibitors. "SARS-CoV-2 uses the SARS-CoV receptor ACE2 for entry and the serine protease TMPRSS2 for S protein priming.

A. Hybrid Alphavirus-SARS-CoV-2 Viral Particle

To establish a rapid cell-based SARS-CoV-2 infection system for screening and evaluation of neutralizing antibodies and antiviral drugs, the present inventors developed a new hybrid alphavirus-SARS-CoV-2 viral particle, in which an alphavirus-based RNA genome is enclosed for rapid expression of reporter genes in target cells (FIG. 1A).

Pseudoviruses and virus-like particles (VLPs) have been widely used for SARS-CoV-2 drug discovery and vaccine development. Pseudoviruses, such as those derived from lentivirus and vesicular stomatitis virus, can mimic the entry process of SARS-CoV-2. However, structurally, they are very different from SARA-CoV-2 and lack structural components provided by M, E, and N of SARS-CoV-2. VLPs closely resemble SARS-CoV-2 particles, but VLPs contain no genome for reporter expression in target cells[35].

Below, the present inventors describe the development and validation of a novel hybrid system, the Ha-CoV-2 particle, which is structurally a VLP, but possesses the ability of a pseudovirus to enter and express reporter genes in target cells. The genome of Ha-CoV-2 is derived from alphavirus, which allows for rapid and robust quantification of reporter expression within hours of viral entry. As explained below, it was demonstrated that Ha-CoV-2 can be used for rapid screening and quantification of neutralization antibodies, viral variants, and antiviral drugs.

In one embodiment, the genomic RNA consists of the 5' untranslated region and open-reading frames coding for the nonstructural proteins (nsp) 1-4 (nsp1-4) from Semliki Forest virus (SFV)[16,29]; the inclusion of nsp1-4 allows for self-amplification of the RNA genome in cells. The RNA genome also contains viral subgenomic RNA promoters for the expression of reporter genes (such as luciferase). The 3' end of the genome contains the 3' untranslated region of SFV and a poly(A) tail that are used to stabilize RNA. In addition, a putative SARS-CoV-2 packaging signal was inserted downstream of the reporter gene to facilitate RNA packaging by the SARS-CoV-2 structural protein N.

To assemble viral particles, the DNA vector, Ha-CoV-2, was used to express the genomic RNA. The Ha-CoV-2 vector was co-transfected with vectors expressing the structural proteins of SARS-CoV-2 (S, M, E, and N) into HEK293T cells (FIG. 1A). Virion particles were harvested at 48 hours post cotransfection, and tested for virion infectivity and the ability to express reporter genes in target cells.

First, to confirm the presence of the SARS-CoV-2 structural proteins in Ha-CoV-2 particles, western blots of purified particles were performed, using antibodies against the S protein of SARS-CoV-2 the presence of S was detected in Ha-CoV-2 particles (FIG. 1B).

To further determine the presence of the other structural proteins of SARS-CoV-2, Ha-CoV-2 particles were assembled using FLAG-tagged M and N proteins, and performed western blots using anti-FLAG antibodies. The presence of both M and N were detected in Ha-CoV-2 particles (FIGS. 1C and 1D).

Furthermore, to determine whether these structural proteins are present in the same virion particles, anti-S antibody-conjugated magnetic beads were used to pull down Ha-CoV-2 particles. The magnetically separated particles were further probed with western blot using the anti-FLAG antibody for the presence of FLAG-tagged M protein. As shown in FIG. 1E, the presence of M was detected in the anti-S antibody pull-down particles, confirming that cotransfection of the SARS-CoV-2 structural proteins with the Ha-CoV-2 vector led to the production of SARS-CoV-2 virus-like particles (VLPs).

B. Ha-CoV-2(GFP) Reporter Virus

To further demonstrate the ability of Ha-CoV-2 particles to infect and express reporter genes in target cells, an Ha-CoV-2(GFP) reporter virus was assembled, and used to infect HEK293T(ACE/TEMPRSS2) cells that overexpressed both ACE2 and TMPRSS2.

GFP expression was observed in cells following infection (FIG. 2A), demonstrating that the alphavirus-based RNA genome can be packaged by the budding SARS-CoV-2 VLPs, and is capable of expressing the GFP reporter gene in target cells.

To determine whether the infection of target cells by Ha-CoV-2 is dependent on the interaction of S with the ACE2 receptor[18,30], an Ha-CoV-2(Luc) reporter virus was assembled and used to simultaneously infect HEK293T (ACE/TEMPRSS2) cells and the parent HEK293T cell. As shown in FIG. 2B, Ha-CoV-2(Luc) expressed high-levels of Luc in the HEK293T(ACE/TEMPRSS2) cells but minimal levels of Luc in HEK293T, demonstrating the requirement of ACE2 for Ha-CoV-2 infection.

To further confirm the requirement for S-ACE2 interaction, particles were generated without the S protein. As shown in FIG. 2C, in the absence of S, Luc expression was highly diminished, demonstrating the requirement of S for Ha-CoV-2 infection. The requirement for the other structural proteins, M, N, and E, were also tested for Ha-CoV-2 infection. Although these proteins were found to be nonessential, removal of M, N, and E led to a reduction in Ha-CoV-2 infection (FIG. 2C). In investigating the contributions of M, N, and E for Ha-CoV-2 infection, it appeared that, in general, particles assembled with two or three of these structural proteins gave rise to a higher level of infection than those with only one protein. However, the presence of S plus E appears to be sufficient for the full infectivity of Ha-CoV-2 (FIG. 2D).

A major advantage of utilizing alphavirus-based RNA genome for Ha-CoV-2 is the extremely fast speed and high-level gene expression of alphaviruses; gene expression from the subgenomic RNA promoters occur within hours of infection, and levels of viral plus-RNAs can reach 200,000 copies in a single cell[16,28]. Following the time course of Ha-CoV-2(Luc) infection, it was observed that the Luc reporter expression increased rapidly within 6 hours from the addition of particles to cells (FIG. 3). This rapid reporter expression kinetics permits use of Ha-CoV-2 for fast screening and quantification of neutralization antibodies and antiviral drugs.

C. Comparison Between Ha-CoV-2 and Lenti-Pseudovirus

Lenti-based SARS-CoV-2 pseudoviruses have been commonly used for antiviral drug screening and neutralization antibody assays[10,14]. A comparison was performed of Ha-CoV-2 with lenti-pseudovirus for the infection of both ACE2-overexpressing cells and cells expressing native levels of ACE2. Lenti-pseudovirus and Ha-CoV-2 particles were assembled in similar cell culture conditions, and an equal volume of the particles was used for infection. Both lenti-pseudovirus and Ha-CoV-2 can infect the ACE2-overexpressing HEK293T(ACE2/TMPRESS2) cells (FIG. 4A). However, infection of Calu-3, a human lung cancer cells expressing native levels of ACE2, was minimal with the lenti-pseudovirus[31], whereas Ha-CoV-2 particles produced much higher signal for the infection of Calu-3 cells (FIG. 4B). Infection of primary human ACE2-null monkey kidney cells with Ha-CoV-2 did not generate signals above uninfected cell background (FIG. 4C). These results demonstrate that Ha-CoV-2 is likely more sensitive for the infection of low ACE2-expressing cells.

Furthermore, an infection time course of Ha-CoV-2 was followed, and compared with the infection course of the lenti-pseudovirus. As shown in FIG. 4D, in Ha-CoV-2 infection, Luc reporter expression became detectable as early as 2 to 4 hours, whereas in the lenti-pseudovirus infection, Luc reporter expression was detectable only after 24 hours. In addition, the reporter expression in Ha-CoV-2 infection was much more robust; by 24 hours, it reached a level approximately 150 fold higher than that generated from the lenti-pseudovirus infection.

A direct comparison between Ha-CoV-2 and a lenti-pseudovirus was also performed in antibody neutralization assays. While both systems are effective in quantifying neutralizing antibodies, the sensitivity of the two systems differ. The lenti-pseudovirus contains only the S protein of SARS-CoV-2, whereas in some embodiments Ha-CoV-2 contains all four structural proteins (S, M, E, and N) of SARS-CoV-2, and has no structural proteins from other viruses (e.g. gag and pol of lentivirus). Of course, it is understood that in other embodiments, an instant Ha-CoV-2 may comprise only one structural protein (S, M, E, and N) of SARS-CoV-2. In other embodiments, an instant Ha-CoV-2 may comprise two or more structural protein (S, M, E, and N) of SARS-CoV-2. In yet other embodiments, an instant Ha-CoV-2 may comprise three or more structural protein (S, M, E, and N) of SARS-CoV-2. For example, and in no way limiting, in one embodiment, an instant Ha-CoV-2 may comprise S. In another embodiment, an instant Ha-CoV-2 may comprise S and E. In other embodiments, an instant Ha-CoV-2 may comprise S, E, and M proteins, or it may comprise S, E, and N proteins. In other embodiments, an instant Ha-CoV-2 may comprise S, E, M, and N.

Although S is the primary requirement for viral entry, the presence of other structural proteins of SARS-CoV-2 may also affect virion infectivity and particle interaction with cell membrane and antibodies. In the present system, the lack of M and E on virion particles does appear to affect virus infection (FIG. 2D).

In addition to viral structural proteins, virion particles also incorporate multiple cellular proteins during virion budding and release. Many of these cellular factors such as PSGL-1 can impact virion infectivity[15,36-38] and antibody binding to plasma membrane[39]. SARS-CoV-2 budding occurs mainly at the membranes of ER-Golgi intermediate compartment[40], whereas the lenti-pseudovirus buds from the plasma membrane[41]. Because of the difference, it is possible that different sets of cellular proteins may be incorporated into lenti-pseudovirus and SARS-CoV-2. In this regard, the close resemblance of Ha-CoV-2 particle to SARS-CoV-2 may provide a unique tool for studying effects of virion host proteins in SARS-CoV-2 infection and pathogenesis[15].

D. Ha-CoV-2 for Rapid Screening and Quantifying Neutralizing Antibodies

Figure 5:
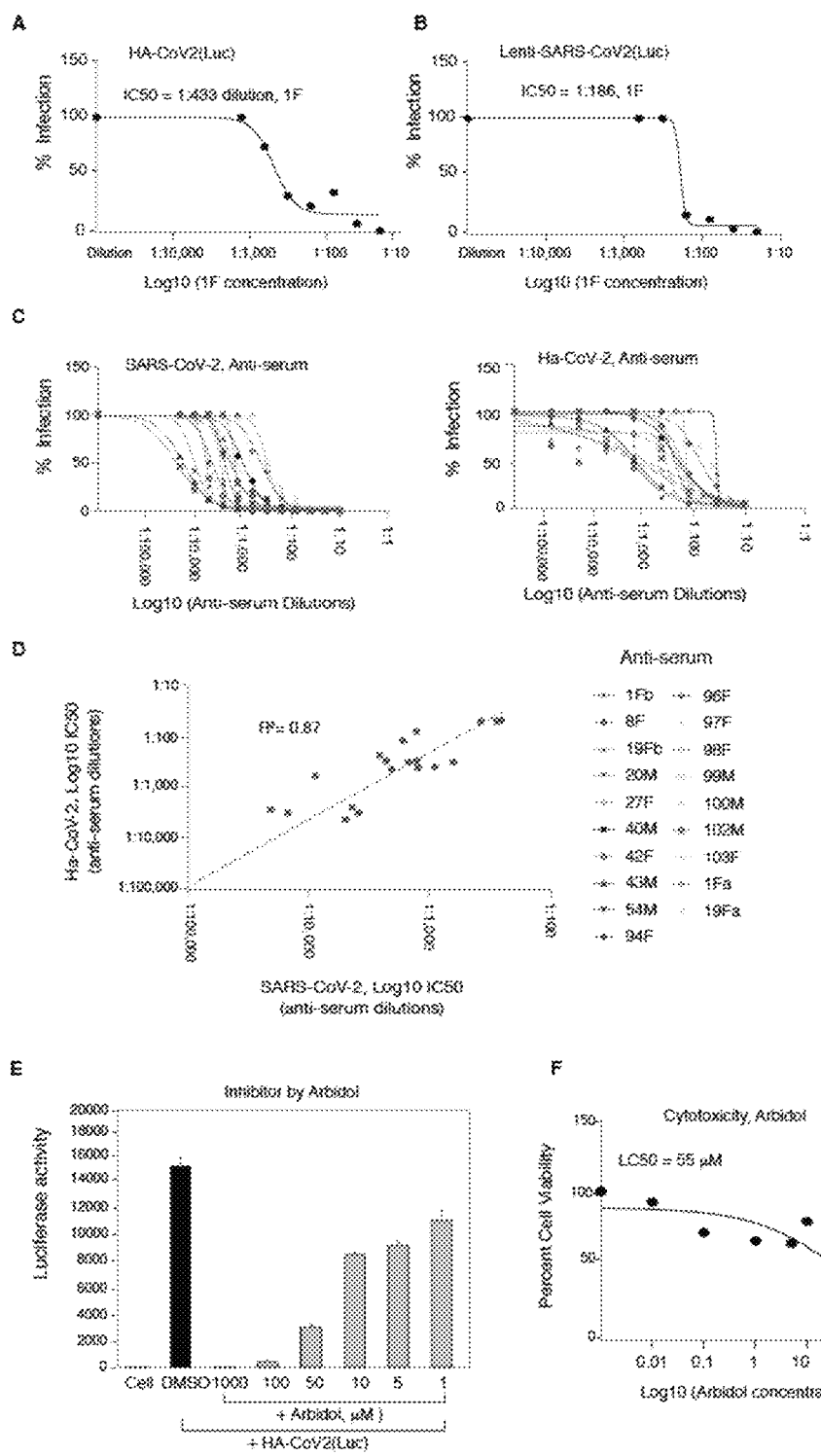
FIG. 5: Validation of Ha-CoV-2 particles for rapid screening and quantification of neutralizing antibodies. (A) Quantification of neutralizing antibodies with Ha-CoV-2 particles. Shown are the concentration-dependent inhibition of Ha-CoV-2(Luc) by the anti-serum 1F and the 1F inhibition curve. 1F was serially diluted and incubated with Ha-CoV-2(Luc) particles for 1 hour at 37° C. The Ha-CoV-2(Luc)-antibody complex was used to infect HEK293T(ACE2/TMPRSS2) cells. Neutralization activities were quantified by luciferase assay at 5 hours post addition of virus to cells. Control serum was from healthy, uninfected donors. The $IC_{50}$ was calculated using the relative percentage of infection versus serum concentration. (B) For comparison, the anti-serum 1F was also similarly quantified using a SARS-CoV-2 S protein pseudotyped lentivirus, Lenti-CoV-2(Luc). Neutralization activities were quantified with luciferase assay at 72 hours post infection. (C and D) Correlation of serum neutralization activities quantified with Ha-CoV-2 (Luc) and SARS-CoV-2. Convalescent plasma from 19 donors was quantified using infectious SARS-CoV-2 and plaque assays, or Ha-CoV-2(Luc). Neutralization activities were plotted and the $IC_{50}$ values were calculated. The correlation in $IC_{50}$ was plotted. (E and F) Rapid quantification of the anti-SARS-CoV-2 activity of Arbidol. HEK293T (ACE2/TMPRSS2) cells were pretreated for 1 hour with Arbidol. Cells were infected with Ha-CoV-2(Luc) in the presence of Arbidol. Viral entry inhibition was quantified by luciferase assay at 5 hours. An MTT cytotoxicity assay of Abidol was also performed on cells (F).

To validate Ha-CoV-2 for rapid screening and quantification of neutralizing antibodies, an anti-SARS-CoV-2 antiserum (1F) was tested, which was serially diluted and pre-incubated with Ha-CoV-2(Luc). The antibody-virus complex was used to infect cells for 5 hours for Luc expression. As shown in FIG. 5A, 1F concentration-dependent inhibition of Ha-CoV-2(Luc) was observed, and the IC50 was determined to be at 1:433 dilution (FIG. 5A). Given that SARS-CoV-2 lenti-pseudoviruses have been widely used in neutralization assays[4,8,14], a similar assay was performed using 1F and a lenti-pseudovirus, Lenti-SARS-CoV-2(Luc)[15]. Infected cells were analyzed at 72 hours post infection. Similar 1F concentration-dependent inhibition of the lenti-pseudovirus was observed, and the IC50 was found to be at 1:186 dilution (FIG. 5B). These results demonstrated that Ha-CoV-2 is as effective as lenti-pseudoviruses for quantifying neutralizing antibodies, but with a much faster speed (5-12 hours versus 48-72 hours).

Based on the 1F results described above, additional validation of Ha-CoV-2-based neutralizing assays were performed using convalescent plasma from 19 donors. The inhibition curve and $IC_{50}$ of each serum are presented in FIG. 5C. For comparison, an independent quantification was conducted using infectious SARS-CoV-2 to validate these anti-sera. A direct correlation ($r^2=0.87$) was observed in the $IC_{50}$ values obtained from Ha-CoV-2 and from SARS-CoV-2 (FIG. 5D). These results demonstrated that Ha-CoV-2 can be used for rapid quantification of neutralizing antibodies.

Pseudoviruses have also been commonly used for high throughput screening of SARS-CoV-2 entry inhibitors[7,10]. As such, a broad-spectrum viral entry inhibitor, Arbidol (Umifenovir)[32], was used for its ability to block Ha-CoV-2 (Luc) infection. As shown in FIG. 5E, dosage-dependent inhibition of Ha-CoV-2(Luc) was observed in 5 hours, and the $IC_{50}$ was determined to be 16 µM. These results demonstrated that Ha-CoV-2 can be used for rapid screening of SARS-CoV-2 entry inhibitors.

E. Ha-CoV-2 for Rapid Evaluation of Relative Infectivity of Viral Variants

As SARS-CoV-2 continues to circulate and evolve, viral variants pose a particular challenge for the control of the COVID-19 pandemic, as documented in the recent emergence of the B.1.1.7 lineage in UK[42]. Viral mutation may lead to increases in viral transmission and fitness, and thus there is an urgent need for rapid identification and characterization of emerging variants for changes in viral infectivity and responses to neutralizing antibodies. The instant Ha-CoV-2 system may provide a robust platform for rapid quantification of viral variants and potential impacts on neutralizing antibodies and vaccine effectiveness.

Figure 6:
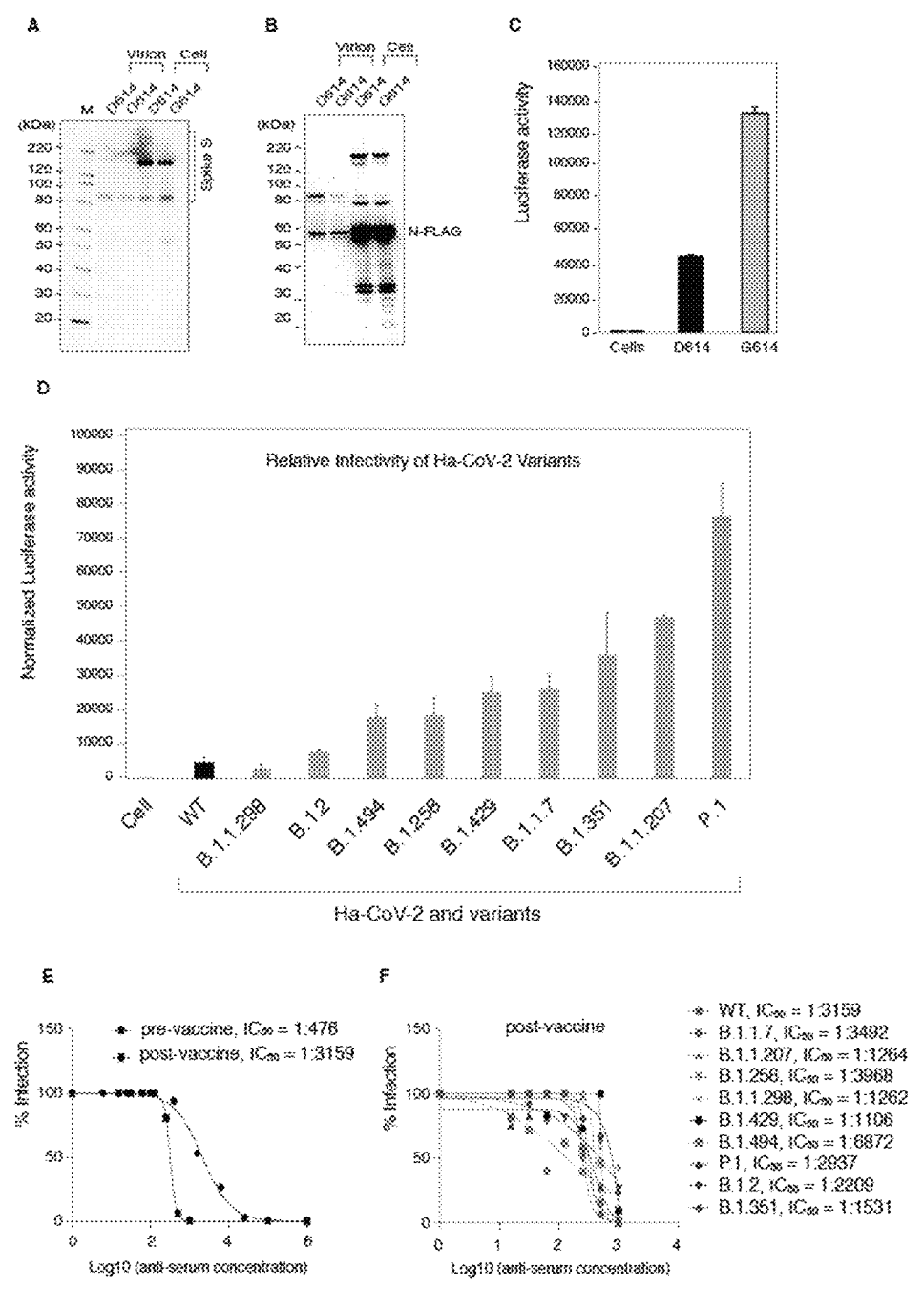

The instant Ha-CoV-2 system was tested for rapid evaluation of relative infectivity of viral variants. The D614G spike mutation emerged early in the COVID-19 pandemic, and has recently been reported to confer greater infectivity that has led to the global dominance of the D614G mutant in circulation[33,34]. To determine whether the increase in virus infectivity can be recapitulated and quantified by the Ha-CoV-2 system, Ha-CoV-2 particles were assembled using the G614 mutant S protein (G614) or the parental S protein (D614). It was found that the D614G mutation did not increase virion release or the level of S protein virion incorporation (FIGS. 6A and 6B). However, Ha-CoV-2 particles bearing the G614 spike were found to be nearly 3 times more infectious than those bearing the D614 spike (FIG. 6C).

Nine Ha-CoV-2(Luc) isolates derived from circulating SARS-CoV-2 variants (selected from the GISAID global reference database, Table 1) were assembled, including the Brazil variant (P.1), the South Africa variant (B.1.351), the UK variant (B.1.1.7), the California variant (B.1.429), and several other emerging variants (B.1.2, B.1.494, B.1.1.207, B.1.258, and B.1.1.298). Ha-CoV-2(Luc) and the related S protein variants were used to infect target cells, and the relative infectivity was quantified.

TABLE 1

List of S protein mutations in SARS-CoV-2 isolates

| GISAID Variant lineage | Mutations in S protein | GISAID Accession number |
|---|---|---|
| B.1.1.7 | A570D, D614G, D1118H, H69del, N501Y, P681H, S982A, T716I, V70del, Y145del | EPI_ISL_581117 |
| B.1.1.207 | D614G, E484K, P681H | EPI_ISL_778908 |
| B.1.1.298 | D614G, H69del, I692V, M1229I, V70del, Y453F | EPI_ISL_616802 |
| B.1.2 | D614G, E484K, G446V, Y453F | EPI_ISL_833413 |
| B.1.258 | D614G, H69del, N439K, V70del | EPI_ISL_755592 |
| B.1.351 | A243del, A701V, D80A, D215G, D614G, E484K, K417N, L242del, L244del, N501Y | EPI_ISL_678597 |
| B.1.429 | A222V, D614G, L452R, S13I, W152C | EPI_ISL_847764 |
| B.1.494 | A262S, D614G, D796Y, H49Y, L452R, N501Y, P681R, Q613H | EPI_ISL_826591 |
| P.1 | D138Y, D614G, E484K, H655Y, K417T, L18F, N501Y, P26S, R190S, T20N, T1027I, V1176F | EPI_ISL_833136 |

* SARS-CoV-2 lineage identification and variant naming were obtained from GISAID (https://www.gisaid.org); mutations in the spike protein and the sequence accession number of each isolate are listed.

As shown in FIG. 6D, when normalized with the genomic RNA copies, these variants in general are 2-10 fold more infectious than the original parental Ha-CoV-2(Luc). These results demonstrated that Ha-CoV-2 can provide a convenient tool for rapid monitoring and quantification of viral variants. As a proof-of-concept, the ability of an anti-serum to neutralize viral variants was quantified. Convalescent plasma was acquired from a donor who was infected, and then vaccinated with one dose Moderna mRNA-1273. This one dose vaccination has greatly increased the anti-serum titer for approximately 6-fold (FIG. 6E). Furthermore, when Ha-CoV-2(Luc) variants were tested, it was found that the post-vaccination serum had neutralizing activities against all variants tested (FIG. 6F). Nevertheless, the neutralizing activities differ greatly among the variants; the anti-serum has the highest neutralizing activity against B.1.494 ($IC_{50}$ 1: 6872), and lowest activity against the B.1.1.429 variant ($IC_{50}$ 1:1106).

These results demonstrate that Ha-CoV-2 can be used for rapid quantification of SARS-CoV-2 variants for potential impacts on neutralizing antibodies and vaccine effectiveness.

F. Ha-CoV-2 Methodology

An instant Ha-CoV-2 particle can be used for a variety of applications, including but not limited to (1) drug screening against COVID entry; (2) drug screening against alphavirus replicase entry, (3) for measuring antibodies, and (4) stimulating an immune response in a subject in need thereof.

For instance, an instant Ha-CoV-2 particle could be used for measuring a subject's antibodies against a panel of SARS-CoV-2 variants, as a means for determining and providing a personalized medicine treatment for the subject. For example, a given subject may have antibodies for some SARS-CoV-2 variants, such as the Brazil variant (P.1), the South Africa variant (B.1.351), and the UK variant (B.1.1.7), but the subject may not have antibodies, for instance, for the California variant (B.1.429), and several other emerging variants (B.1.2, B.1.494, B.1.1.207, B.1.258, and B.1.1.298).

In another example, a subject may wish to have antibodies tested before traveling to a specific country, such as the United Kingdom where the UK variant (B.1.1.7) is the dominant variant. Of course, the location and predominant variant may change with time, and so one of ordinary skill in the art would know to test the predominant variant in a specific location or geography, at the relevant time. In this way, an instant Ha-CoV-2 particle could be used for measuring a subject's antibodies against SARS-CoV-2 variants known in a given geography, as a means for determining and providing a personalized medicine treatment for the subject before traveling. In this regard, and if the subject does not have neutralizing antibodies against a particular variant, then the subject could receive an antibody, vaccine, or treatment before traveling to the specific location, country, or geography.

In another embodiment, an instant Ha-CoV-2 particle may be used for screening drugs and other small molecules that inhibit viral entry. For example, one could determine if a compound blocks viral entry, by:

a) obtaining a compound selected from the group consisting of a viral entry inhibitor, a neutralizing antibody, or antiviral protein or drug;
b) incubating the compound with an instant hybrid particle;
c) introducing the incubated hybrid particle into a cell comprising ACE2; and
d) detecting reporter gene expression in said cell, wherein reporter gene expression is indicative of infecting the cell.

The following Examples are illustrative and do not limit the disclosure. Indeed, various modifications, in addition to those shown and described herein, will become apparent to those skilled in the art from the foregoing description and fall within the scope of the present disclosure.

Example 1: Virus and Viral Particle Assembly

The study of SARS-CoV-2 requires high-level containment that limits the use of infectious virus in common clinical and research laboratories. Pseudoviruses and virus-like particles (VLPs) have been widely used for SARS-CoV-2 drug discovery and vaccine development. Pseudoviruses, such as those derived from lentivirus and vesicular stomatitis virus, can mimic the entry process of SARS-CoV-2. However, structurally, they are very different from SARA-CoV-2 and lack structural components provided by M, E, and N of SARS-CoV-2. VLPs closely resemble SARS-CoV-2 particles, but VLPs contain no genome for reporter expression in target cells[35].

Below, the present inventors describe the development and validation of a novel hybrid system, the Ha-CoV-2 particle, which is structurally a VLP, but possesses the ability of a pseudovirus to enter and express reporter genes in target cells. The genome of Ha-CoV-2 is derived from alphavirus such as Semliki Forest virus (SFV), Chikungunya virus (CHIKV), or Venezuelan Equine Encepalitis virus (VEEV), which allows for rapid and robust quantification of reporter expression within hours of viral entry. As explained below, it was demonstrated that Ha-CoV-2 can be used for rapid screening and quantification of neutralization antibodies, viral variants, and antiviral drugs against SARS-CoV-2 and alphavirus, as well as stimulating an immune response.

The SARS-CoV-2 S, S(D614G), M, E, or N expression vectors were purchased from Sinobiological. The Ha-CoV-2(Luc) and Ha-CoV-2(GFP) vectors, and the S protein variants were selected from isolates identified in the GISAID global database (Table 1), and synthesized by Twist Bioscience. Ha-CoV-2 particles were assembled by cotransfection of HEK293T cells in 10 cm dish with 2.5 μg of each of the SARS-CoV-2 structural protein expression vectors (S, N, E, M) and 10 μg of Ha-CoV-2(Luc) or Ha-CoV-2(GFP). Particles were harvested at 48 hours post cotransfection, filtered through a 0.45 μm filter, and then concentrated by gradient centrifugation.

Lenti-pseudovirus was assembled by cotransfection of HEK293T cells with SARS-CoV-2 S expression vector (0.5 μg), pCMVΔR8.2 (7.5 μg), and pLTR-Tat-IRES-Luc (10 μg) as previously described[15].

Example 2: Detection of Ha-CoV-2 Virion Incorporation of Structural Proteins

The SARS-CoV-2 M-FLAG and N-FLAG vectors were used as disclosed in Zhang et al. A systemic and molecular study of subcellular localization of SARS-CoV-2 proteins. *Signal Transduct Target Ther* 5, 269, doi:10.1038/s41392-020-00372-8 (2020).[43]. HEK293T cells were co-transfected with 10 μg Ha-CoV-2(Luc), 2.5 μg of the SARS-CoV-2 S expression vector, and 2.5 μg each of the M-FLAG, N-FLAG, and E-FLAG vectors. Particles were harvested, filtered through a 0.45 μm filter, and then purified by gradient centrifugation. Virion lysates were analyzed by SDS-PAGE and western blot using Spike Protein S2 Monoclonal Antibody (1A9) (Invitrogen) (1:1000 dilution) or DYKDDDDK Tag Monoclonal Antibody (FG4R) (Invitrogen) (1:1000 dilution). Membranes were then incubated with Anti-mouse IgG, HRP-linked Antibody (Cell signaling) (1:2000 dilution) for 60 min at room temperature. Chemiluminescence signal was detected by using West Pico or West Femto chemiluminescence reagent (Thermo Fisher Scientific). Images were captured with a CCD camera (FluorChem 9900 Imaging Systems) (Alpha Innotech). Particles were also captured with magnetic beads for analyses. Briefly, magnetic Dynabeads Pan Mouse IgG (Invitrogen) ($2\times10^7$ beads/50 µl) were conjugated with Spike Protein S2 Monoclonal Antibody (1A9) (Invitrogen) (2 µl antibody) for 30 minutes at room temperature. After conjugation, virions were incubated with the anti-S2-beads for 30 minutes at 4° C., and pulled down with a magnet. After washing with cold PBS for 5 times, virions were lysed in LDS lysis buffer (Invitrogen). Lysates were analyzed by SDS-PAGE and western blot using DYKDDDDK Tag Monoclonal Antibody (FG4R) (Invitrogen) (1:1000 dilution) to detect FLAG-Tagged SARS-CoV-2 M proteins.

Example 3: Viral Infectivity Assay

Ha-CoV-2 particles were used to infect HEK293T(ACE2/TMPRSS2) cells (a gift from Virongy LLC, Manassas, Va.), Calu-3 cells (ATCC), HEK293T cells (ATCC) and primary monkey kidney cells provided by Dr. Xuefeng Liu. Briefly, cells were seeded in 12-well plates ($2\times10^5$ cells) per well. Cells were infected for 1-2 hours at 37° C., washed, cultured in fresh medium for 3-48 hours, and then lysed in Luciferase Assay Lysis Buffer (Promega) for luciferase activity using GloMax Discover Microplate Reader (Promega). Lentipseudovirus particles were used to infect HEK293T(ACE2/TMPRSS2) cells and Calu-3 cells (ATCC). Cells were infected for 2 hours, cultured for 3 days, and then lysed in Luciferase Assay Lysis Buffer (Promega) for luciferase assays using GloMax Discover Microplate Reader (Promega).

Example 4: Neutralizing Antibody Assay

Ha-CoV-2 particles were pre-incubated with serially diluted sera from COVID19 patients for 1 hour, and then added to HEK293T(ACE2/TMPRSS2) cells for 2 hours. Cells were then washed, and cultured in fresh medium for additional 3-24 hours. Cells were lysed in Luciferase Assay Lysis Buffer (Promega) for luciferase assays using GloMax Discover Microplate Reader (Promega). For neutralization assays using wild-type SARS-CoV-2 virus, anti-serum was serially diluted (a twelve-point, two-fold dilution series starting at 1:10 dilution), and pre-incubated with 100 pfu of SARS-CoV-2 for 1 hour at 37° C. After incubation, viral plaque assay was conducted to quantify viral titers. Briefly, Vero cells (ATCC) in 12-well plates ($2\times10^5$ cells per well) were infected with virus for 1 hour at 37° C. After infection, a 1:1 overlay, consisting of 0.6% agarose and 2×EMEM without phenol red (Quality Biological), supplemented with 10% fetal bovine serum (FBS) (Gibco), was added to each well. Plates were incubated at 37° C. for 48 hours. Cells were fixed with 10% formaldehyde for 1 hour at room temperature, and then the agarose overlay was removed. Cells were stained with crystal violet (1% CV w/v in a 20% ethanol solution). Viral titer of SARS-CoV-2 was determined by counting the number of plaques.

Example 5: Antiviral Drug Assay

Arbidol-hydrochloride (Sigma) was resuspended in Dimethyl sulfoxide (Sigma). HEK293T(ACE2/TMPRSS2) cells were pretreated for 1 hour with serially diluted Arbidol. Ha-CoV-2 particles were added cells, followed by the addition of Abidol to maintain the drug concentration. Cells were infected in the presence of Arbidol for 2 hours, washed, and then cultured in fresh medium for a total of 5 hours. Cells were lysed in Luciferase Assay Lysis Buffer (Promega) for luciferase assays using GloMax Discover Microplate Reader (Promega).

Example 6: Hybrid Particles for Rapid Detection and Quantification of Neutralizing Antibodies Patient serum samples were harvested from donor blood by centrifugation. HAVS(Luc) particles (also called Ha-CoV-2) were incubated with anti-serum (1:60 dilution) for one hour at 37° C., and then used to infect HEK293T (ACE2+TMPRSS2) cells for 5 hours. Neutralization activities were measured by luciferase assay. Serum from uninfected, health donors are used as a control. Dosage-dependent inhibition of the anti-serum 1F was quantified using HAVS(Luc) particles. The inhibition cure was generated by serial dilution (a series of 1:2 dilutions) of serum and incubation with HAVS(Luc) particles for 1 hour at 37° C. The HAVS(Luc)-antibody complex was used to infect HEK293T(ACE2+TMPRSS2) cells for 5 hours. Neutralization activities were measured by luciferase assay. The IC50 was calculated using the relative percentage of the infection and relative log of serum concentration. For comparison, dosage-dependent inhibition of the anti-serum 1F was quantified using SARS-CoV-2 S pseudotyped lentiviruse (LTR-Tat-Luc). The inhibition cure was generated by serial dilution (a series of 1:2 dilutions) of serum and incubation with LTR-Tat-Luc pseudovirus for 1 hour at 37° C. The pseudovirus-antibody complex was used to infect HEK293T(ACE2+TMPRSS2) cells for 72 hours. Neutralization activities were measured by luciferase assay. The IC50 was calculated using the relative percentage of the infection and relative log of serum concentration (as illustrated in FIGS. 5A-D).

Example 7: First Generation and Second Generation SFV Replicon

Figure 7:
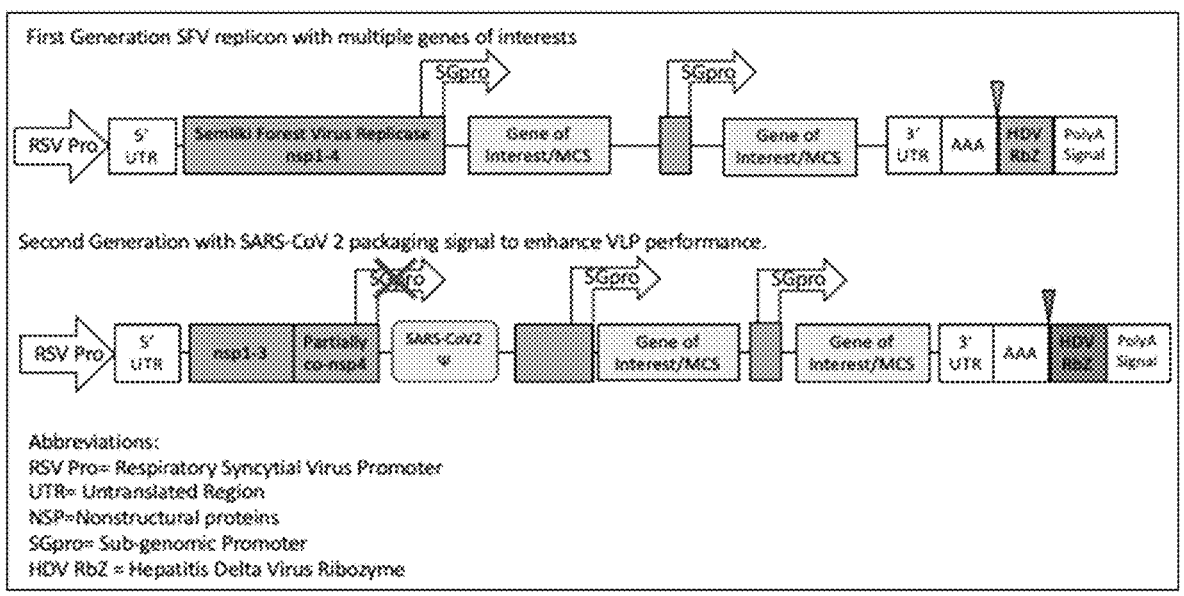
FIG. 7: First Generation and Second Generation Replicons. (A) First generation SFV replicon with multiple genes of interest. Shows first generation of the single-cycle Alphavirus replicons from Semiliki Forest virus (SFV). (B) Second generation with SARS-CoV 2 packaging signal to enhance VLP performance. Second generation of the SFV replicon produced, which will include the SARS-CoV-2 packaging signal to enhance the VLPs and reduce the amount of empty particles.

As shown in FIG. 7, the first generation of the single-cycle Alphavirus replicons from Semiliki Forest virus (SFV) which is produced from a plasmid encoding an eukaryotic promoter which generates a viral RNA with the 5' untranslated region, non-structural proteins(nsp) 1-4 and the transgene driven by the viral subgenmoic promoter. To ensure efficient RNA replication by the viral replicase a polyA tail is encoded directly from the plasmid and is cleaved by the hepatitis delta virus ribozyme. A second subgenomic promoter is added to the replicon to allow for multiple transgenes to be produced. Co-transfection of the SFV replicon and the SARS-CoV-2 structural components will generate hybrid VLPs. The SFV replicon produces an abundance of replicon RNA that can hijack the budding SARS-CoV-2 VLPs.

A second generation of the SFV replicon will be produced which will include the SARS-CoV-2 packaging signal to enhance the VLPs and reduce the amount of empty particles. This should greatly enhance the infection signal and further reduce the incubation times needed for infection assays. To ensure the full genomic replicon is packaged the SARS-CoV-2 packaging signal is inserted just after a codon optimized NSP4 protein (partially co-NSP4). The codon optimization destroys the original sub-genomic promoter which is then replaced downstream of the packaging signal. The packaging signal of SARS-CoV-2 can also be inserted at either the 5' end, internal, or 3' end of the Ha-CoV-2 genomes.

Example 8: Large Scale Production

To meet the demands of the current pandemic this technology will need to move to large scale production. Previous studies have shown that stable cell lines that generate VLPs can be difficult to produce typically due to cytotoxic effects from the over production of viral structural proteins. To overcome this challenge a cell line can be produced that will only produce the structural components of the VLPs when a functioning replicon is present. Previous studies have demonstrated efficient VLP production from stable cell lines by using Alphavirus replicon dependent genomes. These defective replicons do not package and only produce genes from the sub genomic promoters when a separate functional replicon is present.

Figure 2:
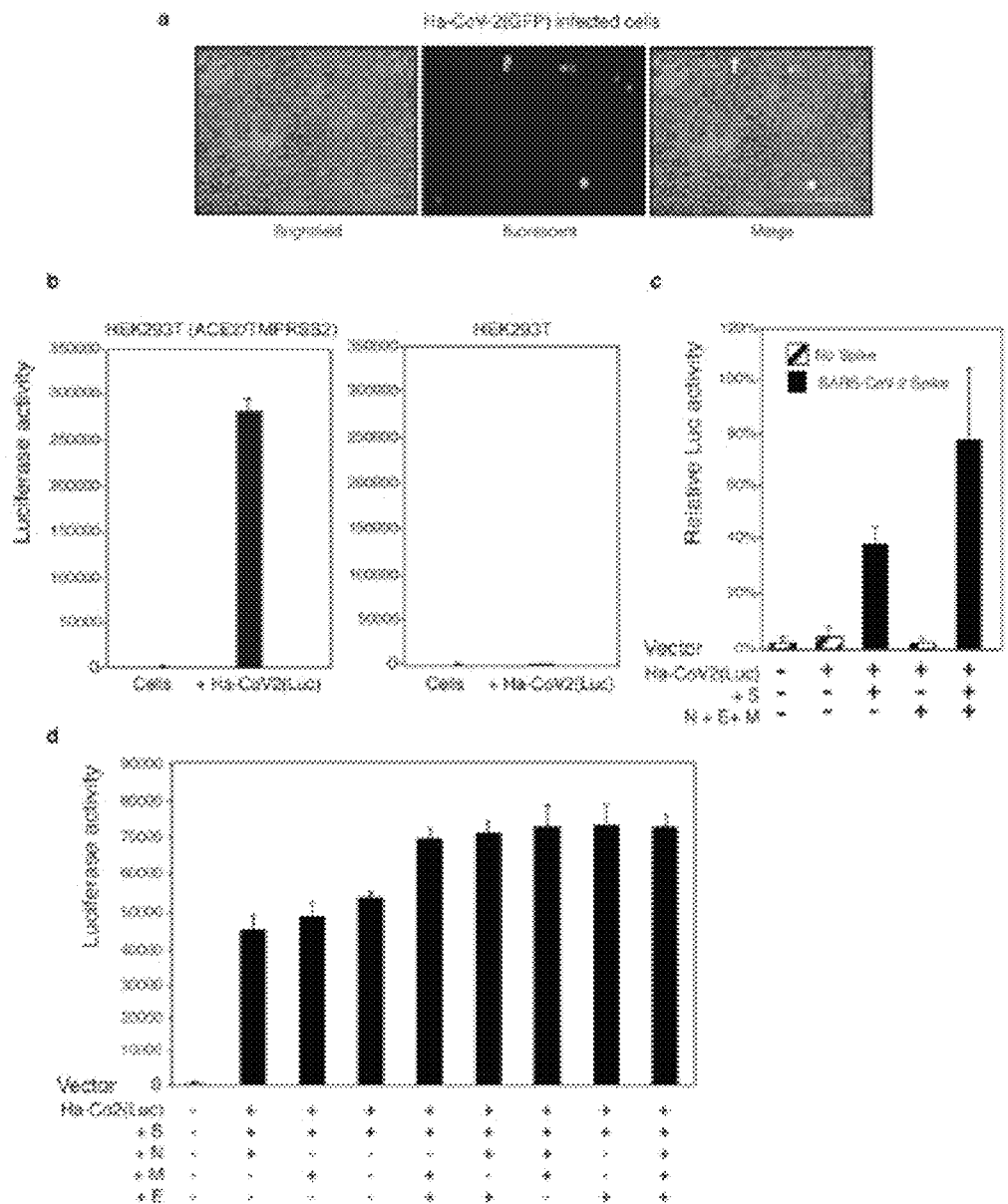
FIG. 2: SARS-CoV-2 S protein and ACE2-dependent infection of target cells by Ha-CoV-2. (A) HEK293T(ACE2/TMPRSS2) cells were infected with Ha-CoV-2(GFP) particles. GFP expression was observed 48 hours post infection. (B) ACE2-dependent infection of target cells by Ha-CoV-2 (Luc). HEK293T(ACE2/TMPRSS2) and HEK293T cells were infected with Ha-CoV-2(Luc) particles. Luciferase expression was quantified at 24 hours post infection. (C) SARS-CoV-2 S protein-dependent infection of target cells by Ha-CoV-2(Luc). Particles were assembled in the presence or absence of S or M+E+N. Luciferase expression was quantified at 4 hours post infection. (D) Requirements of M, E, and N for optimal infectivity of Ha-CoV(Luc). Particles were assembled in the presence S and combinations of individual proteins of M, E and N. Luciferase expression was quantified. Assays in (B) to (D) were performed in triplicates.
Figure 3:
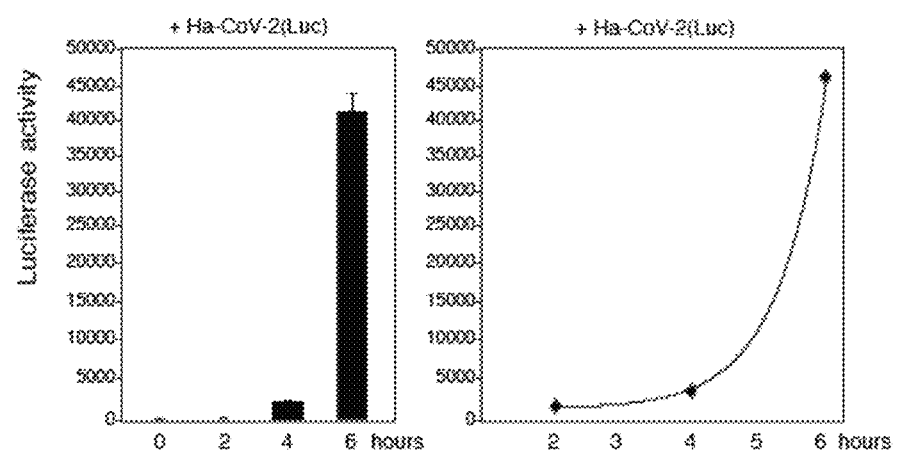
FIG. 3: Rapid time course of reporter gene expression in Ha-CoV-2(Luc) infection. A 6-hour time-course of luciferase expression following infection of HEK293T(ACE2/TMPRSS2) cells with Ha-CoV-2(Luc) particles. Cells were infected with Ha-CoV-2(Luc) for 2 hours, washed, cultured in fresh medium, and then lysed and analyzed for Luc expression at different time points. The addition of virus to cells was defined as time "0". Infection assays were performed in triplicates.
Figure 4:
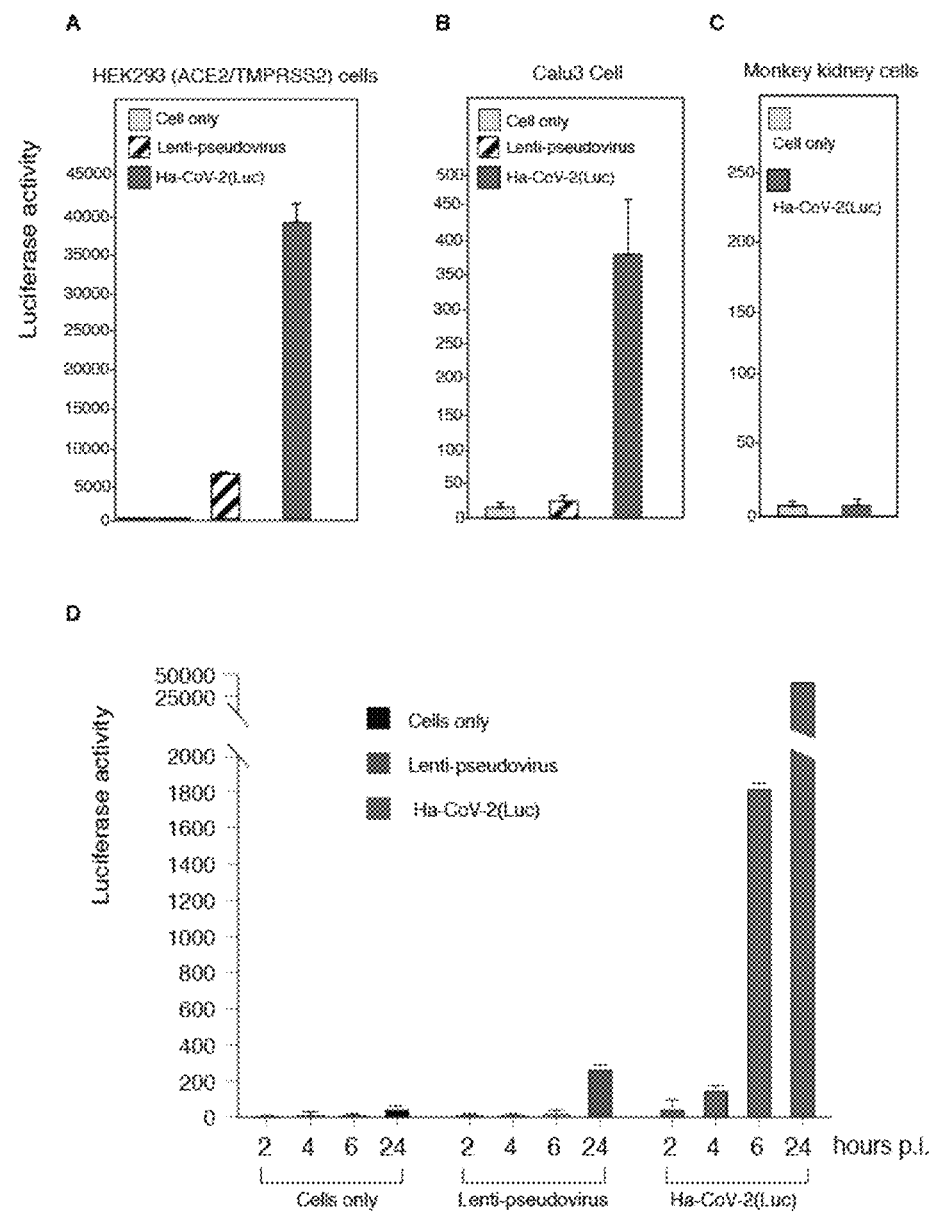
FIG. 4: Comparison of SARS-CoV-2 S pseudotyped lentivirus with Ha-CoV-2 particles. (A to C) HEK293T (ACE2/TMPRSS2) and Calu-3 cells were infected with an equal volume of viral particles, Lenti-CoV-2(Luc) or Ha-CoV-2(Luc). Relative infection was quantified by luciferase assay at 72 hours post infection. Primary monkey kidney cells were also infected with Ha-CoV-2 for comparison. (D) Comparison of lenti-pseudovirus and Ha-CoV-2 in an infection time course. HEK293T(ACE2/TMPRSS2) were infected with an equal volume of viral particles, lenti-CoV-2(Luc) or Ha-CoV-2(Luc). Relative Luc reporter expression was quantified by luciferase assay from 2 to 24 hours post infection. All infection assays were performed in triplicates.

In present application as shown in FIG. 2, the cell lines will allow for these hybrid VLPs to be produced in large quantities for greater use in commercial and clinical applications.

To demonstrate the function of the hybrid VLPs a permissible cell line, HEK293T-ACE2, was infected the production of green fluorescent protein was monitored using fluorescent microscopy. The hybrid VLP was able to produce the gene of interest in target cells. Below are microscope images which show HEK293T-ACE2 cells infected by a hybrid VLPs with a replicon. A second infection with the hybrid VLPs was performed on a permissible HEK293T-ACE2+TMPRSS2 cell line. The replicon encodes a luciferase gene and luciferase activity was measured three days post infection. The hybrid VLPs are an improved method for modeling SARS-CoV-2 entry and a new platform for antiviral and vaccine discovery.

To demonstrate the function of the hybrid VLPs a permissible cell line, HEK293T-ACE2, was infected the production of green fluorescent protein was monitored using fluorescent microscopy. The hybrid VLP was able to produce the gene of interest in target cells. FIG. 2 is microscope images which show HEK293T-ACE2 cells infected by a hybrid VLPs with a replicon.

A second infection with the hybrid VLPs was performed on a permissible HEK293T-ACE2+TMPRSS2 cell line. The replicon encodes a luciferase gene and luciferase activity was measured three days post infection as shown in FIGS. 2B-C. The hybrid VLPs are an improved method for modeling SARS-CoV-2 entry and a new platform for antiviral and vaccine discovery.

What is claimed is:

1. A hybrid particle, comprising:
   a) a RNA genome derived from an alphavirus from a first plasmid; and
   b) at least one SARS-CoV-2 structural protein derived from a second plasmid differing from the first plasmid, wherein said structural protein is a spike protein (S), a membrane protein (M), an envelope protein (E), and the nucleocapsid protein (N); and
   wherein the hybrid particle is a hybrid pseudovirus, which is assembled and produced in a producer cell by co-transfection of the producer cell with the first plasmid and the second plasmid or plasmids.

2. The hybrid particle of claim 1, wherein the particle is a non-replicating particle.

3. The hybrid particle of claim 1, wherein the RNA genome derived from the alphavirus comprises a reporter gene or a gene of interest.

4. The hybrid particle of claim 1, wherein the RNA genome comprises:
   a) 5' untranslated region;
   b) an open-reading frame coding for a non-structural proteins (nsp) 1-4;
   c) a reporter gene or a gene of interest;
   d) 3' untranslated region; and
   e) a poly(A) tail.

5. The hybrid particle of claim 4, further comprising a SARS-CoV-2 packaging signal, wherein the SARS-CoV-2 packaging signal is downstream of the reporter gene.

6. The hybrid particle of claim 1, wherein the hybrid particle is SARS-CoV-2 virus-like particles (VLPs).

7. The hybrid particle of claim 3, wherein the reporter gene comprises a GFP gene or a luciferase gene.

8. The hybrid particle of claim 1, wherein the hybrid particle targets a cell expressing ACE2.

9. The hybrid particle of claim 1, comprising two SARS-CoV-2 structural proteins, wherein said structural proteins comprise S and E.

10. The hybrid particle of claim 1, comprising four SARS-CoV-2 structural proteins, wherein said structural proteins comprise S, E, M, and N.

11. The hybrid particle of claim 10, wherein the hybrid particle has a direct correlation in a IC50 value with SARS-CoV-2.

12. A method, comprising:
   (a) co-transfecting a first vector encoding at least one SARS-CoV-2 structural protein and a second vector comprising an RNA genome derived from an alphavirus, wherein the alphavirus RNA genome comprises (i) a DNA promoter at a 5' end, (ii) a first untranslated region, (iii) an open reading frame coding a nonstructural protein from an alphavirus, (iv) a reporter gene, (v) a SARS-CoV-2 packaging signal sequence, (vi) a viral subgenomic RNA promoter, (vii) a gene of interest, (viii) a second untranslated region, and (ix) a polyA tail; and
   (b) generating the hybrid particle of claim 1.

13. The method of claim 12, further comprising infecting a target cell with the hybrid particle, wherein said target cell expresses ACE2.

14. The method of claim 12, wherein expression of the reporter gene is capable of producing a signal that facilitates detection and quantification of an infection.

15. The method of claim 14, wherein the signal is read after about 2 to about 72 hours following infection by the hybrid particle.

16. A method for detecting a subject's antibody response to one or more SARS-CoV-2 variants, comprising
   a) incubating a serum sample from said subject with the hybrid particle of claim 10;
   b) introducing the incubated hybrid particle into a cell comprising ACE2; and
   c) detecting reporter gene expression in said cell, wherein
   reporter gene expression is indicative of the subject having no neutralizing antibodies to block viral infection of the cell, and
   no reporter gene expression is indicative of the subject having antibodies that block viral infection of the cell.

17. A composition comprising the hybrid particle of claim 1.

18. The composition of claim 17, wherein said composition is a vaccine or a particle that can initiate an immune response.

19. A composition comprising the hybrid particle of claim 10.

20. A composition comprising the hybrid particle of claim 19, wherein said composition is a vaccine or a particle that can initiate an immune response.

* * * * *